United States Patent [19]
Frese, Jr.

[11] Patent Number: 4,892,709
[45] Date of Patent: Jan. 9, 1990

[54] MICRODEVICE FOR GAS AND VAPOR SENSING

[75] Inventor: Karl W. Frese, Jr., Cupertino, Calif.

[73] Assignee: SRI International, Menlo Park, Calif.

[21] Appl. No.: 104,338

[22] Filed: Oct. 2, 1987

[51] Int. Cl.⁴ .................... H01L 7/00; H01C 13/00
[52] U.S. Cl. .................................. 422/98; 422/83; 338/34; 338/35
[58] Field of Search .................. 422/83, 98; 338/34, 338/35; 73/23, 25, 26, 26 R, 29

[56] References Cited

U.S. PATENT DOCUMENTS

| | | | |
|---|---|---|---|
| 4,041,437 | 8/1977 | Matsuura et al. | 422/98 |
| 4,378,691 | 4/1983 | Terada et al. | 338/35 |
| 4,482,581 | 11/1984 | Lorin et al. | 338/35 |
| 4,651,121 | 3/1987 | Furubayashi et al. | 338/35 |
| 4,723,439 | 2/1988 | Asakura et al. | 338/35 |

Primary Examiner—Barry S. Richman
Assistant Examiner—T. J. Wallen
Attorney, Agent, or Firm—Fliesler, Dubb, Meyer & Lovejoy

[57] ABSTRACT

In accordance with the present invention a microdevice 10 is set forth for gas sensing. The microdevice 10 includes a conductive substrate 12 having an insulator layer 14 on a surface 16 thereof, the insulator layer 14 having an opening 18 therethrough exposing a portion 20 of the surface 16. A conducting member 22 is in contact with the insulator layer 14. The member 22, the insulator layer 14 and the portion 20 of the surface 16 define an ionization chamber 28. Gas can flow through the ionization chamber 28. A potential difference is applied between the substrate 12 and the member 22. The current flowing between the substrate 12 and the member 22 is measured. A microdevice 10 as disclosed herein uses very little power and has very high sensitivity.

23 Claims, 2 Drawing Sheets

$$i = \sigma(E)\pi d t E$$

MICRODEVICE FOR GAS AND VAPOR SENSING

TECHNICAL FIELD

The present invention relates to a microdevice for gas and vapor sensing. More particularly, the invention relates to a device which senses the change in conductivity across a miniature ionization chamber formed in an insulating layer upon a semiconductor.

BACKGROUND ART

The miniaturized gas detectors of the prior art are such that water vapors or films cannot be tolerated on their active surfaces. As a result, heaters are incorporated in or used with the devices to keep the system dry. For example, L. Treitinger, P. Tischer and B. Schneider-Gmelch, in U.S. Pat. No. 4,338,281, issued July 6, 1982, show the use of highly doped silicon, doped until it is essentially metallic, to act as a resistance heater. Silicon dioxide is used to separate the silicon heater from the active metal oxide which may be, for example, $SnO_2/PdO$. Because of the intimate contact in the silicon heater and the active oxide ($SnO_2$), low power consumption results. This low power consumption is, however, of the order of 0.1 watt per $mm^2$ and is still higher than would be desirable.

As another example, M. Kimura, in U.S. Pat. No. 4,343,768, issued Aug. 10, 1982 sets forth a sensor heater design which provides relatively low power consumption. Silicon dioxide is used in the construction of the sensor in that a silicon dioxide film completely separates two conducting phases, namely the silicon phase and the platinum or palladium catalyst. The Kimura patent, like the Tretinger, et al patent, utilizes a heater structure so as to exclude both liquid water and water vapor. The power consumption is not specified but appears to be about the same as that in the Tretinger, et al structure. This is because both of the structures require heating which is significantly power consumptive.

A microdevice for gas and vapor sensing which would not require the use of a heater to exclude water and water vapor and which also was highly sensitive would provide a significant step forward over the background art just discussed.

The present invention is directed to overcoming one or more of the problems as set forth above.

DISCLOSURE OF INVENTION

In accordance with an embodiment of the present invention a microdevice is set forth for gas sensing. The microdevice includes a substrate having an insulator layer on a surface thereof, the insulator layer having an opening therethrough exposing a portion of the surface. A conducting member is in contact with the insulator layer. The member, the insulating layer and the exposed portion of the surface define an ionization chamber. Means are provided for flowing gas through the ionization chamber. Means are provided for applying a voltage difference between the substrate and the member. Means are provided for measuring the current flowing between the substrate and the member.

A microdevice in accordance with the present invention does not require the use of a heater since it does not require the exclusion of water vapor and, indeed, must utilize adsorbed water, or a similar adsorbed solvent to provide its gas sensing function. Furthermore, since a heater is not present the amount of energy utilized by the microdevice is generally orders of magnitude less than that utilizing the before discussed prior art devices. Still further, in accordance with preferred embodiments of the invention the ionization chamber of the microdevice of the present invention can be kept so small that extreme sensitivity results for various gaseous analytes.

BRIEF DESCRIPTION OF DRAWINGS

The invention will be better understood by reference to the figures of the drawings wherein like numbers denote like parts throughout and wherein.

BEST MODE FOR CARRYING OUT INVENTION

Figure 1:
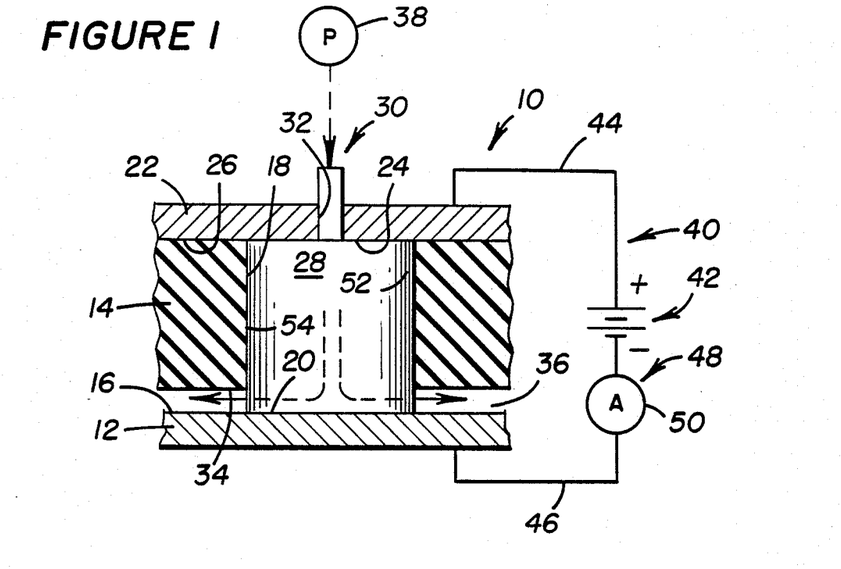
FIG. 1 illustrates, schematically, a microdevice for gas sensing in accordance with an embodiment of the present invention.
Figure 2:
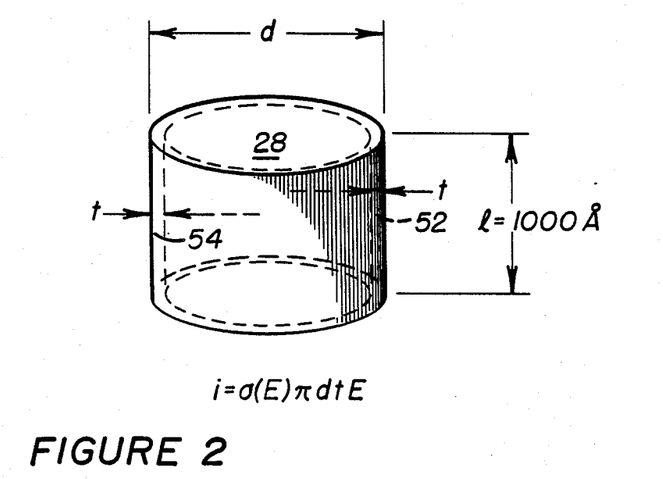
FIG. 2 illustrates, schematically, the ionization chamber portion of the embodiment of FIG. 1.

A microdevice 10 in accordance with an embodiment of the present invention is illustrated in FIGS. 1 and 2. The microdevice 10 includes a conducting substrate 12, for example, p-silicon, having an insulator layer 14 on a surface 16 thereof, the insulator layer 14 having an opening 18 therethrough which exposes a portion 20 of the surface 16 of the substrate 12.

Another conducting member 22, for example, also made of doped silicon, is in contact with the insulator layer 14 in generally parallel relationship with the substrate 12. The member 22, specifically at area 24 of a surface 26 of the member 22, along with the insulator layer 14 and the portion 20 of the surface 16, serves to define an ionization chamber 28.

Means 30 is provided for flowing gas through the ionization chamber 28. In the embodiment illustrated the means 30 includes an inlet hole 32 through the member 22 and a pair of outlet conduits 34,36 through the insulator layer 14. The gas flow can be through the impetus of diffusion or a pump 38 can be utilized to provide a pressure differential to speed the flow. Also, while flow is shown as being in through the hole 32 and out through the conduits 34,36, the direction of flow can be in other directions, for example in through the conduits 34,36 and out through the hole 32, in through one of the conduits 34,36 and out through the hole 32 and the other of the conduits 34 and 36, or the like. Also, the two conduits 34 and 36 can be replaced with a single such conduit or with more than two such conduits. Still further, there can be more than one entry hole such as the hole 32.

Means 40 is provided for applying a voltage difference between the substrate 12 and the member 22. In the particular embodiment illustrated the voltage applying means is simply a battery 42 along with appropriate conductors 44,46.

Means 48 are provided for measuring the current flowing between the substrate 12 and the member 22. In the particular embodiment illustrated the current flow measuring means is simply in the nature of an ammeter 50 in series with the battery 42.

The substrate 12 in accordance with the present invention will preferably comprise a semiconductor material. This allows the formation of the insulating layer 14 by oxidation or nitridation, or by deposit of an oxide, a nitride, or another insulating material, to provide as the insulator layer 14 a silicon dioxide or silicon nitride layer. The conducting member 22 can be a semiconductor material, for example doped silicon, gallium arsenide, or silicon carbide, or can be a conductive material, for example a metallic conductor. For ease of construction it is generally the case that both the substrate 12 and the conducting member 22 are semiconductor materials, generally silicon or silicon carbide. The more preferred embodiments are those wherein both the substrate 12 and the conducting member 22 are silicon and the insulating layer 14 is silicon dioxide and wherein the substrate 12 and the conducting member 22 are silicon carbide and the insulating layer is silicon nitride, particularly $Si_3N_4$.

It should be particularly pointed out that the sizes of the various components and of the ionization chamber 28 as shown in FIG. 1 are not even approximately to scale. That is, the insulating layer 14 is generally significantly thinner than will be the substrate 12 and the conducting member 22. FIG. 2 shows an ionization chamber 28 which is round in cross-section. However, the ionization chamber 28 can be square, rectangular, or any other shape in cross-section. The following discussion will assume the circular cross-section shown but only for purposes of discussion.

As is illustrated the ionization chamber 28 is shown as having an outer diameter, d, and a length, l. Also seen in FIG. 2 is a layer 52 adsorbed on the walls 54 of the chamber 28. The layer 52 is in the nature of a relatively thin film of liquid, usually water, but generally any liquid which can support ionic conductivity when certain chemicals, for example the gaseous species being detected by the microdevice 10, are dissolved in it. Indeed, the presence of the liquid layer 52 is essential to the operation of the microdevice 10. The liquid layer 52 is generally provided by simple adsorption of gas from the surrounding atmosphere. That is, the moisture in the air is absorbed or adsorbed onto the wall 54 to form the liquid layer 52. In certain instances it may be advisable to utilize humidifiers or otherwise introduce sufficient moisture into the atmosphere so as to provide the layer 52.

The diameter, d, or the greatest lateral dimension if the cross-section is not circular, can be of any convenient size. For example, excellent results has been obtained when the diameter is approximately one centimeter. The thickness of the liquid layer 52 may vary somewhat but generally falls in a range from about 10 to about 200 Angstroms, and is usually about 50 to 100 Angstroms. The length, l, can also vary considerably, but is preferably relatively short. Generally, the length, l, will be no more than, at most, about 10,000 Angstroms, more preferably no more than 5,000 Angstroms, and still more preferably no more than about 2,000 Angstroms. Excellent results have been obtained with a length, l, of 1,000 Angstroms.

While FIG. 1 shows only use of a battery 42 and an ammeter 50, it should be noted that additional circuitry may be present for processing the signals to come up with a final reading that indicates concentration of a desired species in the gaseous phase. Furthermore, the needed circuitry can be readily integrated by integrated circuitry (IC) techniques onto the substrate 12 and/or the member 22, in the instance when at least one of these is a semiconductor material, for example silicon.

Because of the method of construction of the microdevice 10 the ionization chamber 28 can be made very small and the length of the ionization chamber, l, can be made very small. This provides very high electric fields across the ionization chamber, generally fields of at least about $10^4$ volts per centimeter, and even up to as much as about $10^7$ volts per centimeter. This amplifies the current response. As a result, the microdevice 10 is capable of sensing gases at $10^{-9}M$ or better in the gas phase. Indeed, utilizing this device detection of hydrogen chloride vapor at $5 \times 10^{-11}M$ has been demonstrated. The selectivity of response of the microdevice 10 is based on the solubility and dissociation constant, at prevailing field strength, in the chosen stationary liquid phase 52 at the surfaces of the electrode and via the use of derivatized electrode surfaces.

While not being bound by theory it is believed that it would be advantageous to set forth an understanding of the theory by which it is believed the microdevice 10 operates. A number of gaseous species, when contacted with the liquid layer 52 will dissolve therein to provide, for example, an acidic solution. As the microdevice 10 will respond to $H^+$ in water at concentrations of $10^{-7}M$ or higher, one can expect to detect such gaseous materials in low concentrations. The main requirement is that the gas, when it dissolves in the liquid 52, be that liquid 52 water or another medium, produces ions above the background level due to solvent auto ionization or impurity level.

The extent of ionization of weakly ionizing species is controllable by controlling the magnitude of the applied field. Thus, selectivity can be provided. An array of microdevices 10 operating at different applied fields can also provide information about the chemical classification of unknown compounds by determining the dependence of the response (conductivity) on field strength in a given solvent. An array of sensors with different adsorbed solvents can provide selectivity.

To avoid confusion, the terms solvent or "stationary phase" refer to the water film or other substance adsorbed on the ionization chamber walls 54. The "mobile phase" or analyte is the gas to be detected, and the "support" is the electrode surfaces, 20 and 24, forming opposite faces of the ionization chamber 28.

Referring to FIG. 1 it will be seen that gas enters the hole 32, which may be, for example, 1 mm in diameter, which is formed in a member 22, for example by use of a diamond drill, and then exits through the channels 34,36 which are etched in the silicon dioxide layer 14. The electric field is applied to the substrate 12 and the member 22, and ionic current flow occurs in the liquid film 52. The conductivity of the water layer is about $5 \times 10^{-8}$ per ohm.centimeter. The conductivity of the silicon dioxide layer is about $10^{-16}$ per ohm.centimeter. Accordingly, the current flow is overwhelmingly confined to the liquid film 52. In addition to the good insulating properties of silicon dioxide, its dielectric breakdown field strength is about 2 to $3 \times 10^7$ volts per centimeter. These two unique properties make silicon dioxide an insulating material of choice for the microdevice 10. $Si_3N_4$ or silicon dioxide formed on semiconducting silicon carbide crystals generally shares such advantages. The availability of single crystal silicon and the optimal native oxide currently make it the material of choice.

The microdevice 10 has been tested with air carrier gas and with analyte gases including ammonia, various amines, and hydrogen chloride. To date, $5 \times 10^{-11}$ moles of ammonia and $1 \times 10^{-14}$ moles of hydrogen chloride have been detected. These amounts correspond to gas phase concentrations of $10^{-7}$ and $10^{-11}$ moles per liter respectively. The response has been shown to be dependent on sample size and to increase with electric field strength. The gas phase concentration of $10^{-9}$M corresponds to 0.1 milligram per cubic meter for a compound of molecular weight 100.

It is believed that the microdevice 10 operates on the principle of electrolytic conductivity change. Because humid air circulates through the high field region in the chamber 28, a thin water film 52 forms on the wall 54. The electric field probably enhances the extent of water adsorption because of the lower free energy of a water dipole in the high field region. When a gas enters an adjacent chamber 28 it dissolves in the liquid layer 52 and undergoes chemical changes leading the formation of ions. For example:

$$HCN \underset{}{\overset{H_2O}{\rightleftarrows}} H^+ + CN^- \quad (1)$$

$$R-X + H_2O \underset{}{\overset{hydrolysis}{\rightleftarrows}} R-OH + HX \quad (2)$$

and if R—OH and HX are acidic $$ROH \rightleftarrows RO^- + H^+ \quad (2a)$$

$$HX \rightleftarrows H^+ + X^- \quad (2b)$$

In the first example, Eq. (1), $CN^-$ and $H^+$ ions are formed by simple dissociation. In Eqs. (2) to (2b) R—X is hydrolyzed and the products undergo acid dissociation.

It is advantageous if the electric field strength (voltage difference) is large enough to increase the concentration of ions, over zero field, by a factor of at least 10, preferably at least 100. Generally field strengths of at least about $10^4$ V/cm, more preferably at least about $10^5$ V/cm and still more preferably at least about $10^6$ V/cm, are suitable for accomplishing this.

The HCN molecule is a very weak acid in $H_2O$, having a $pK_a$ of 9.2 at zero electric field. However in the microdevice 10, the extent of dissociation of HCN is enhanced by the electric field so that at $4 \times 10^6$ V/cm, $pK_a = 6.2$ and at $1 \times 10^7$ V/cm, $pK_a = 3.2$. Thus up to $10^6$ times increase in the dissociation constant of an acid or base occurs in the microdevice 10. The electric field also enhances the dissociation of species like ROH and HX. The field also exerts a catalytic effect on the chemical step of hydrolysis, Eq. (2). This is based on the general Bronsted Catalysis rule, which states that rate of a reaction depends on the free energy change. As the electric field stabilizes the ionic species, $\Delta G$ becomes more negative and the activation energy for hydrolysis is decreased. According to the theory of Onsager, the rate constant for the dissociation step is increased to the same degree as the equilibrium constant. This effect is discussed for detection of Soman and mustard in a later section.

The first of two modes of operation is the electrolysis mode. When a thin film of water is placed in a strong electric field as in the microdevice 10, several electrochemical processes occur. First the $H_2O$ is electrolyzed to $O_2$ and $H_2$ according to the following reactions:

$$H_2O \rightleftarrows OH^- + H^+ \quad (3)$$

-continued $$\text{at p-type} \quad OH^- + 1h^+ \leftarrow \tfrac{1}{2}O_2 + H^+ \quad (4)$$

$$\text{at n-type} \quad 2H^+ + 2e^- \longrightarrow H_2 \quad (5)$$

The mechanisms of these reactions are not known for wet silicon surfaces, but considering the large voltage applied to the microdevice 10, the rates are rapid enough so that the electron transfer steps are not rate limiting. Because the electrolysis involves removal of ions from the analyte gas by redox processes as well, the microdevice 10 is rapidly reversible in this mode. Electron transfer steps involving the dissolved gas are not shown.

The second important process involves migration of the $H^+$ and $OH^-$ ions to the cathode and anode to maintain charge balance. The ionic current for this process controls the current in the microdevice 10. This is expected because intrinsic water is being considered, that is, water without added dopants or salts. The conductivity of intrinsic water is governed by the autodissociation reaction, Eq. (3). In the absence of a strong electric field, the conductivity of pure water is about $5.5 \times 10^{-8}$ ohm$^{-1}$cm$^{-1}$ at 25° C. Normal electrolytes in batteries or fuel cells have conductivity of about $10^7$ times larger so that ionic conduction is not current limiting in these cases.

Another mode of operation involves only ionic migration and not electrolysis. This mode can be called the migration mode. If a field too low to cause appreciable water splitting is used, than a stable water film will be held on the detector surface by electrostatic forces in addition to the normal forces of physisorption. If this stationary film is penetrated by an ionizing gas, a conductivity response is observed. In this mode the sensor requires more time to recover because the electrolysis of solute gas and water solvent does not occur due to the low field. In the migration mode the microdevice 10 can accumulate ions and give an integrated response. If a longer response time is allowed, a more dilute gas can be sensed because of integration. The advantages of the migration mode are that nonvolatile stationary phases other than water can be used and response can be integrated.

Detector Current

Detector background current can be calculated when only solvent is present and the current response can be calculated when a dissolved gas is present. The calculation is based on using water as the solvent and an acidic gas. In principle, any solvent combining with an acid, base, or hydrolyzable gas can be used. The goal is to obtain an equation relating the increase in current when the detector equilibrates with a gas at concentration, $C_g$ (moles/liter), in the gas phase. The solvation equilibration, which is rapid for the system, will be discussed separately.

Background Response

Figure 3A:
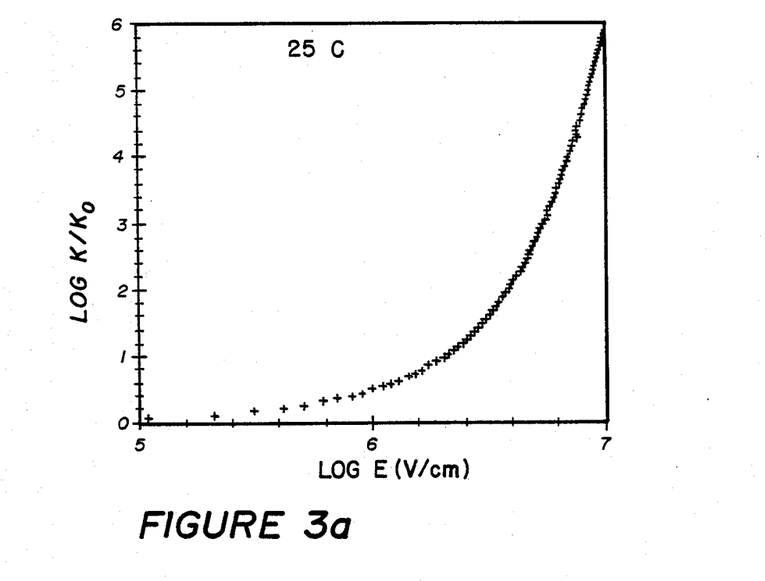
FIGS. 3a, and 3b illustrate, graphically, relative dissociation constants of a weak electrolyte or water as a function of field strength.
Figure 3B:
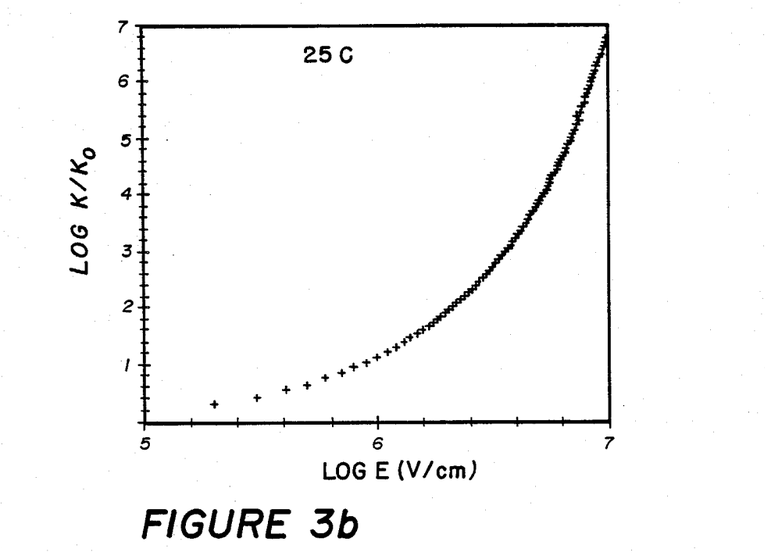

Referring to the geometry in FIG. 2, one has for the background ionic current, $i_o$, under applied field, E (volts/cm), $$i_o = \sigma(E) \cdot t \pi d \cdot E \quad (6)$$

where $\sigma$ and t are the conductivity and thickness of the water layer, respectively, d is the diameter of the ionization chamber, and 1 is $10^{-5}$ cm, the thickness of the $SiO_2$ layer. The term $t\pi d$ measures the cross sectional area of the water film. The conductivity is a function of ion mobility and concentration. However, both mobility and concentration depend on the electric field strength. The most important effect is the enhancement of the ion concentration due to the field dissociation effect. For the case of pure water, the ion concentrations $[H^+]$ and $[OH^-]$ are equal and given by $(K_{wo})^{\frac{1}{2}}=10^{-7}$ M at zero field. In the presence of an electric field the dissociation constant, $K_w$, increases according to the theory given by L. Onsager. FIG. 3 shows plots of the relative dissociation constant vs field strength for either pure water or a weak acid or base dissolved in water. The calculations are cumbersome and require computer solution; therefore, only the results are presented. The field dependence of the dielectric constant of the solvent has to be included in the calculation. Curve A is based on Onsager's model for the dielectric constant, $\epsilon(E)$, of a dipolar liquid in an external field and Curve B refers to Booths results for $\epsilon(E)$ using Kirkwood's theory. It should be noted that the field dissociation effect will be much greater than shown in FIG. 3, if the solvent dielectric constant is 10 or less.

With this theoretical background one can calculate the conductivity for water films $$\sigma(E)=F/1000(\mu_{H^+}+\mu_{OH^-})\cdot 10^{-7}\cdot (K_w/K_{ow})^{\frac{1}{2}} \quad (7)$$

where F=96,487 coul/equivalent. Inserting conventional mobilities, $3.6\times 10^{-3}$ and $2.1\times 10^{-3}$ cm²/volt sec for $H^+$ and $OH^-$, one finds the background current with a water film is $$i=1.72\times 10^{-7} t\cdot E\cdot (K_w/K_{wo})^{\frac{1}{2}} \quad (8)$$

where D was taken as 1 cm. For $1=10^{-5}$ cm, 30 volts applied, and $t=2\times 10^{-7}$ cm, i is calculated to be $8\times 10^{-7}$ amp.

Since the thickness, t, of the water film will depend on humidity of the carrier gas (which could be air), the detector will be sensitive to water content of the carrier gas, thus being usable as a humidity sensor.

In summary, the background current depends on many factors including detector dimensions, applied voltage, water film thickness, extent of dissociation of the solvent and ion mobilities. The background current density will not exceed $\sim 3\times 10^{-7}$ A/cm².

Excess Current Response

The excess current or current above background will be called $\Delta i=i-i_o$. One is concerned with the current due when the detector equilibrates with gas at concentration $C_g$. If the gas, HA, completely dissociates, the current in amps is given by $$i=\frac{F}{1000}(\mu_{H^+}+\mu_{A^-})C\cdot t\pi d\cdot E \quad (9)$$

where C is the concentration HA in the liquid film. In terms of Henry's Law constant, k, and the gas phase concentration, $C_g$ moles/liter, one has at 25° C.

$$\Delta i \simeq F/1000(\mu_{H^+}+\mu_{A^-})\cdot t\pi d\cdot \quad (10)$$

$$\left[\frac{55.5RT}{k}\cdot C_g - 10^{-7}(K_w/K_{wo})^{\frac{1}{2}}\right]\cdot E \text{ Amps}$$

as long as $C\geq 10^{-6}$ M, and $\mu_A-\simeq \mu_{OH^-}$. Eq. (10) shows the excess current is linear with gas concentration.

Inserting the constants used above and assuming $A^-=Cl^-$ $$\Delta \simeq 1.33\ t[1.4\times 10^3\ C_g/k - 10^{-7}(K_w/K_o)^{\frac{1}{2}}]\cdot E \quad (11)$$

Putting typical values of $k=10^{-4}$ atm, $t=2\times 10^{-7}$ cm, $C_g=10^{-9}$ M, and $E=3\times 10^6$ V/cm, one finds $i-i_o=1.1\times 10^{-2}$ Amp. The background current was $8\times 10^{-7}$ Amp. This result shows the detector is capable of very good sensitivity. In fact, for the specific case of HCl, for $i-i=10\times 10^{-6}$ A, one should be able to detect $3\times 10^{-17}$ M HCl vapor.

Another case of practical significance is the type of gas that forms an incompletely dissociated acid in a solvent such as water. When a weak acid at concentration, C, ionizes in water, the $[H^+]$ is given by $$[H^+]\simeq (K_d(C-[H^+]))^{\frac{1}{2}}\simeq (K_aC)^{\frac{1}{2}} \quad (12)$$

provided $[H^+]>>[OH^-]$. The second approximation on the right-hand side is valid if the degree of dissociation is small, i.e., $Ka\lesssim 0.01\ C$. The concentration of $A^-$ will be very close to $[H^+]$ under the assumed conditions. The current is then in analogy to Eq. (10).

$$i=F/1000(\mu_{H^+}+\mu_{A^-})(K_aC)^{\frac{1}{2}}\cdot t\pi d\cdot E \quad (13)$$

and $$\Delta i \simeq F/1000(\mu_{H^+}+\mu_{A^-})\cdot t\pi D\cdot [(K_aC)^{\frac{1}{2}}-10^{-7}(K_w/K_{wo})^{\frac{1}{2}}]\cdot E \quad (14)$$

where the value of $K_a$ is referred to the field strength E. In terms of gas phase concentration, $C_g$, the excess current is, $$\Delta i = F/1000(\mu_{H^+}+\mu_{A^-})\cdot t\pi D\cdot \quad (15)$$

$$\left[\left(K_a^{\frac{1}{2}}\left(\frac{55.5RT}{k}\cdot C_g\right)^{\frac{1}{2}}\right) - 10^{-7}(K_w/K_{wo})^{\frac{1}{2}}\right]\cdot E$$

Using $7\times 10^6$ V/cm, $k=10^{-2}$ atm, and $C_g=10^{-9}$ M, $\Delta i=8\times 10^{-6}$ Amp. The conditions chosen correspond to an acid with a zero field pK of 9.2. The background current would be $3\times 10^{-6}$ Amp. If one assumes Henry's law constant is $\sim 10^{-2}$ atm, then one can sense $\lesssim 0.1$ mg/m³ of the weakly acid gas. If the vapor is a weak base, then an equation similar to (15) applies, but with $K_a$ replaced by $K_b$.

The influence of thermodynamic and physical properties of the system on the absolute response of the sensor has been detailed. The most important parameters are: electric field strength, dissociation constant of the acid or base at a given field, and the solubility of the gas in terms of Henry's law constant. The response of a weak acid or base can be greatly enhanced by the electric field.

There is an absolute detection limit based on thermodynamic properties than can be evaluated by finding the value of $C_g$ that causes $i-i_o$ to vanish in water. The result is $$C_g = 10^{-14}\left(\frac{k}{55.5RTK}\right)$$

where K is the acid or base dissociation constant at zero field and k is Henry's law constant. The weakest acid one might wish to detect might have a $pK_a \sim 9$. The detection limit would then be about $1 \times 10^{-10}$ M if k is 0.01 atm. The limit would decrease linearly as K increases or the Henry's law constant decreases. Note that for strong acids such as HCl, k can be as low as $10^{-9}$ atm. On the other hand, for fixed gas such as $O_2$ and $N_2$, k is about $10^4$ atm. Therefore, gases will be rejected by the microdevice 10 on the basis of solubility. Both acid/base strength and solubility have major influences on detector response. The electric field variable can be used to amplify the response of a weakly dissociating gas by means of the field dissociation (Second Wein effect, FIG. 3).

In the above discussion, the first Wein effect was omitted, which will also serve to amplify the detector response. In essence, the ion mobility depends on field strength because the ionic atmosphere (solvation sheath) cannot move with a sufficiently fast moving ion. An "unsolvated" ion is more mobile. In the calculations zero field ion mobilities were used, and thus better responses are expected than those calculated above. The correction for the first Wein effect amounts to a factor of 2-3 increase for $\Delta i$ at $10^6$ V/cm.

The calculations have also been limited to $H_2O$ solvent. On one hand, other polar solvents with low autoionization constants should give much lower background currents. For example, methanol and ethanol have $K_i = 2 \times 10^{-17}$ and $3 \times 10^{-20}$ compared to $1.0 \times 10^{-14}$ for $H_2O$. In addition, certain gases of interest may be more or less soluble in these nonaqueous solvents. On the other hand, acidity or basicity may be diminished in a nonaqueous solvent. Such an approach may be useful for fixed detector applications where nonaqueous solvent vapor could be circulated through the microdevice.

Space Charges, Field Strengths, and Thin Films

It will be realized that the ions $H^+$, $OH^-$, or $A^-$ in water will form a space charge in the liquid layer 52. This space charge acts as counter charge to the charge on the surfaces 20,24 of the silicon electrodes 12,22 which cause the electric field. If the counter charge is too close to the silicon electrodes, then the field can be largely diminished within the water film 52, thus leading to decreased sensitivity. As will be demonstrated, the water film thickness is small compared to the space charge layer thickness so that the average field in the $H_2O$ is nearly equal to the applied field, $V/l$.

The parameter of interest is the Debye length, L, (cm), and it is given by $$L=(\epsilon kT/4\pi e^2 n_i)^{\frac{1}{2}} \quad (17)$$

where $\epsilon$ = dielectric constant of water, $e = 4.8 \times 10^{-10}$ esu, n = ions/cm$^3$ and kT is thermal energy. L is the distance that contains the space charge at concentration $n_i$. For water at zero field, L is $1.4 \times 10^{-4}$ cm. At $3 \times 10^6$ V/cm, $L = 6 \times 10^{-5}$ cm. It can be seen that the space charge length is about 300 times longer than the water film thickness of usually 20-50 Angstroms that has been used. This means that the field in the bulk of the water film will be within 90% or better of the applied field for all practical field strengths. This calculation shows an important advantage of using very thin water films. The fast absorption kinetics connected with such thin films is discussed next.

Equilibration Time

The microdevice 10 of the invention is theoretically capable of responding to very weak acids or bases at quite low concentrations, that is, $10^{-9}$ or lower. These calculations are based on thermodynamical limits and the question of rate of response has to be considered. In the system, a gas flows over a thin water layer 52 and the question is: Under what conditions will the system equilibrate? A similar problem arises in the theory of gas-liquid chromatography and the parameter that is sought is H, the height equivalent to a theoretical plate (HETP). H is the distance the carrier gas has to travel so that equilibrium between the absorbed gas and liquid phase obtains. This theory will be applied to the microdevice 10 with the constraint that the length of the "GLC column", is equal to the electrode spacing, namely, $1 \times 10^{-5}$ cm. If the calculated H is less than $10^{-5}$ cm, than the system will be at equilibrium and the above calculations of the absolute response apply. In this discussion the response in the absence of equilibrium has not been estimated.

The possible contributions to H come from (a) diffusion in the stationary phase (water film) and (b) activated adsorption on the liquid surface. Point (a) concerns the resistance to movement of absorbed gas into the bulk of the water film and point (b), perhaps the more important, is related to the difficulty of a gas molecule attaching into the surface of the water.

A property R, called the retention ratio, that appears in the expressions below is defined as the fraction of solute in the gas phase (above the liquid) at equilibrium. Values of R for a 20-Angstroms water film in an ionization chamber with a volume of $10^{-8}$ liter are given in Table 1 for different values of Henry's constant.

Expressions for H for the two processes mentioned above are as follows:

$$H_1 = \tfrac{8}{3}R(1-R)d^2v/D_1 \quad (18)$$

where $D = 2 \times 10^{-7}$ cm, $D_1 = 1 \times 10^{-5}$ cm$^2$/sec and $$H_2 = [8(1-R)^2/a_o^2 c \rho A_w] \cdot v \exp(W/RT) \quad (19)$$

where $a_o$ is the sticking coefficient at infinite temperature (0.1 to 1.0), $\rho$ = density of water, 1 g/cc, $A_w$ is surface area/g of water, $\sim 5 \times 10^6$ cm$^2$/g, and $\bar{c}$ is the gas mean thermal velocity. Also shown in Table 1 are the H values for each Henry's constant. The adsorption step probably limits the response, but using parameter values typical to gas-liquid chromatography it appears that the longest equilibration time would be about 1 microsecond. This would increase by $\sim 1000$ times if the activation energy for adsorption increased to 10 kcal/mole. Physical adsorption does not normally require chemical bond breaking, but only creation of a hole in a liquid surface; thus, W is not expected to be above $\sim \frac{1}{2}$ ($\Delta H$ vap) or about 6 kcal mole for water.

The last column of Table 1 contains the equilibration time that was calculated as the time for the gas to travel the HETP. The calculations are based on a linear velocity of 0.1 cm/sec. These very favorable results demonstrate the great advantage of using ultrathin water films. From Eqs. (18) and (19) D and $A_w$ are obtained, both contributing to small HETP and short equilibration time.

Response time When Hydrolysis Precedes Ionization

As an example of the situation when hydrolysis or elimination precedes acid dissociation, first consider the case of Sarin. From Hildebrand's Rule, the Henry's constant is calculated to be $\sim 6 \times 10^{-4}$ atm. For $10^{-9}$ M in the gas phase, the equilibrium concentration in water would be $2 \times 10^{-3}$ M. According to Gustafson and Martell, the rate constant of hydrolysis in pure $H_2O$ is $5 \times 10^{-5}$ sec$^{-1}$ at zero-electric field. If $10^{-7}$ M is used for the absolute detection limit of ions in the liquid phase, then, according to the integrated second-order rate law, it would take $10^5$ seconds to sense ions from Sarin interacting with pure water. This value has to be reduced due to the removal of products by electrolysis. One cannot quantify this aspect at present. If initial rates are used, it would take 1 to 10 seconds to build up detectable amounts of ions.

However, these calculations ignore several key facts. First, because of water electrolysis, there are pH gradients in the cell. In particular, near the cathode, $H^+$ ions are depleted and in this region the water layer 52 is basic. The higher pH will catalyze the hydrolysis reaction. The most important catalytic effect, however, comes from the influence of the electric field. The slow step in forming HF and phosphoric acid in pure $H_2O$ is (20)

Because a neutral species forms two ions in the rate limiting step, the field will have a large catalytic effect. The rate constants should be increased in about the same ratio as the equilibrium constants. At 3 to $7 \times 10^6$ V/cm, k will be $10^3$ to $10^4$ times larger. Significant increases in rate are predicted and the response time should be on the order of 1 sec or less.

Another example where the electric field is expected to have a significant catalytic effect is in the hydrolysis of mustard gas. The mechanism is SN1 with rate determining step, $k = 2 \times 10^{-3}$ sec$^{-1}$ (21)

At $3 \times 10^6$ V/cm, k should be $\sim 0.5$ sec$^{-1}$. In this case the rates are favorable, but the solubility is poor. Assuming Henry's constant of 0.01 atm and $10^{-9}$ M in the gas phase, the liquid phase concentration would be $2.4 \times 10^{-6}$ M The time required for detectable ion formation in this case will be about 1 second.

Selectivity

The microdevice 10 described is a device that detects the appearance of ions in a liquid stationary phase. In contrast to field ionization processes in the gas phase, chemical electric fields are used to form the ions. These fields derive from the ordinary chemical properties of the materials in the microdevice 10. The chemical effects are enhanced and amplified by the externally applied electric field leading to high sensitivity. Importantly, the same chemical effects lead to selectivity.

The first requirement is that the gas be soluble in the stationary phase (e.g., water or alcohols). The components of air, except water, which is necessary in some applications, do not affect the microdevice 10. This effect gives rise to the first level of selectivity. The parameter of interest here is Henry's constant for gas solubility. Other properties being constant, the larger the Henry's constant for the gas, the smaller the detector response. Various nonvolatile stationary phases other than water can be used to effect solubility selectivity. This strategy has been previously used in gas-liquid chromatography. For example, agents that are insoluble in water may be soluble in certain alcohols. When strong chemical interactions occur, solubility is greatly enhanced, as in the case of HCl in water. It is also probable that the solubility of some gases will be affected by the available external electric field.

Once the gas enters the liquid 52, it must ionize. In many cases, a hydrolysis step occurs that leads to the ionizable species. The extent of ionization, as determined by the dissociation constant at the prevailing external electric field strength, will govern selectivity based on acid/base properties. Other properties being constant, the larger the dissociation constant, the greater the detector response. The hydrolysis products of the G chemical agents are phosphoric acid derivatives and HF. These species will be easy to detect since they are moderately strong acids even in the absence of an electric field. The detection of weak acids may be enhanced by the use of nonionic base, as the stationary liquid phase 52. In such a liquid, many weak acids will dissociate extensively. It is also possible to use the reactivities of liquids other than water to cause a response. As an example, alkylating agents can form quarternary ammonium salts from nitrogen bases. Reaction with hydroxide ions present in neutral or basic water will change the displacement of charged leaving groups (since volatile alkylating agents must be uncharged), causing an increase in ionic conductivity.

Some compounds selected for detection may not readily form ions in the sensor or such formation may be slower than desired. The incorporation of a catalyst to convert the substance into an ionizable compound (perhaps by hydrolysis) offers a flexible way around this difficulty. By appropriate choice of catalysts, this method also offers a way of enhancing selectivity by creating detectable ions from only the molecules that will react with the catalyst.

The catalyst can be located in the gas stream before the sensing unit, and can catalyze a reaction that produces a volatile ionizable species (such as HCl, $CO_2$, $NH_3$), or the catalyst can be in (or under) the conducting film that is in the chamber 28. An example of a catalyst placed before the microdevice 10 is the use of a Pd catalyst at 350° C. to oxidize $CH_4$ to $CO_2$. The $CO_2$ continues on to the chamber 28 and is detected as the acid, $H_2CO_3$, after hydrolysis in the water film 52. Such a system has been used to sense methane.

It has been proposed above that the microdevice 10 use a nonvolatile liquid stationary phase 52 (vide supra). In such a case the catalyst could be dissolved in the liquid 52 to provide an in situ generation of detectable ions. Such supported catalyst solutions have been used previously to catalyze the reactions of gaseous samples as they passed over the catalyst/solvent supported on gas chromatography supports. Another possibility is that the catalyst could be dissolved in a volatile solvent that is removed by evaporation, leaving a thin layer of solid catalyst present on the surface 54. T microdevice 10 is operated as previously described with the water (or other liquid) forming a film 52 on top of the solid catalyst. In this case either the catalyst would need to be soluble in the liquid film 52 or the vapor to be sensed would have to be somewhat soluble in the liquid film 52.

Another method entails covalently anchoring the catalyst on the surface 54. This method offers the advantage that it is not possible for the catalyst to move around in the presence of the electric field and possibly be concentrated at, or be deactivated by, the electrode surfaces 20,24. The chemical derivatization of silicon and silicon dioxide surfaces is well established. Among the reagents commercially available for such chemistry are ligands with functional groups capable of polymerizing surface SiOH groups as shown in Equation (22).

Two usable ligands are N Si(OMe)$_3$ and PH$_2$P Si(OMe)$_3$, both of which are commercially available. Such ligands have been used previously to anchor organometallic compounds onto such surfaces. It is also possible to fairly easily modify many ligands of promising catalysts to provide a site for anchoring. For instance, Cu(II)-EDTA has been shown to catalyze the hydrolysis of Sarin. Such a catalyst should be anchorable by modification of the ligand as shown in Equation (21).

The structure of the catalyst on the surface would be

It has also been found that quaternary ammonium salts catalyze the reaction of phosgene with alcohols to produce HCl. A quaternary ammonium ion, N,N'-bis(3-(trimethoxysilyl)propyl)-4,4-bipyridinium, has been used extensively for derivatizing silicon and silicon dioxide surfaces and should make a good candidate for the detection of phosgene. Although both catalysts are ionic, the positive ions are immobilized and net current cannot flow.

A related method of promoting selectivity is to introduce biologically active materials on the electrode surface 20,24. Immobilized enzymes are an attractive possibility. Squid-DRFase, which can be used to catalyze the hydrolysis of Soman, can be covalent anchored to an agarose resin. The hydrolysis is agarose-catalyzed in neutral pH, consistent with the pH of the water layer 52. Thus, the sensor can fit into biochemically oriented detection schemes.

Power Requirements

The power requirements for the detector element are about $10 \times 10^{-8}$ amps $\times 50$ V $= 50 \times 10^{-7}$ watts/cm$^2$ in a standby-on mode. During actual sensing (ionizing gas present) this could increase to 1–4 watts/cm$^2$ or less for brief periods. Other power requirements depend on whether humid air is passed through the detector by a mini-pump or whether gas reaches the detector by diffusion. In the latter case the power requirements are limited to the above figure of $\sim 1$ $\mu$watt/cm$^2$. In the former case, the pumping power will be approximately $\leq 5 \times 10^{-2}$ watts for a 1 cm$^2$ sensor (10 ml/min, $\Delta p = 10$ psi). Use of a 20 watt-hr rechargeable NiCd battery would allow the pump to be powered for 400 hours. Direct current micropumps measuring 1.5 in. by 1.0 in. by 2 in. are commercially available (from Gillian Instrument Corp). In any case, the device can operate in the room temperature range and thus requires no significant heating input. This is a significant advantage.

The power requirements for integrated currents that might be used for signal processing are on the same order as the pumping power.

Physical Dimensions

One preferred detector element consists of two Si wafers sandwiched together. The area of the electrodes is $\sim 1$ cm$^2$ and the thickness is about 0.2 cm. These are prototype dimensions and the elements can be made smaller. A single element can be made ten times smaller when formed as part of an array on a silicon wafer. Such array wafers can be 1 to 5 cm$^2$ in area and 0.2 to 0.5 cm thick. The relationship between detector current and area and SiO$_2$ thickness is given in Equations (9)–(15).

The invention will be better understood by reference to the following experimental examples.

Experimental Examples

A device was fabricated with a structure similar to that shown in FIGS. 1 and 2. The substrate was p-Si and the conducting member was n-Si, both doped to about $1 \times 10^{15}$ carriers cm$^3$. A 1000 Angstrom SiO$_2$ layer was thermally grown on the p-Si by heating in oxygen for 2 hours. A Kepco power supply and Kiethly 616 were used to bias the device and measure the current response respectively. A Houston 2000 recorder with a time base module was used to record the data. Gas samples were injected into a flowing stream of air saturated with water vapor by means of a gas syringe at a linear velocity of 0.1 ml min$^{-1}$.

Results

Table 1 shows the peak current response, $\Delta i$, for 50 $\mu$l injection contained about $10^{-7}$ moles of trimethylammine. Each 50 $\mu$l injection contained about $10-7$ moles of trimethylammine. In the case of ammonia, the vapor from above a 30% w/w solution was injected. There were approximately $10^{-9}$ moles of ammonia per microliter of vapor injected. The results of these experiments, performed at 50° C., are listed in Table 2. The response, given in column 1, is measured in integrated current or charge in coulombs. The second column in Table 2 gives the sample size in microliters.

In each of the test cases documented below, the test gas gives OH$^-$ ions and either (CH$_3$)$_3$NH$^+$ cations for trimethylammine and ammonia respectively. The data in Table 1 show that the response of the detector increases with the electric field strength in qualitative agreement with the theory. The results in Table 2 shows that the integrated response increases proportional to the sample size, also in agreement with the theory. The sensitivity in coulombs per mole of $NH_3$ was calculated using data in Table 2 and yielded a value of 0.12 coul mole $NH_3$. This projects that $<1\times10^{-11}$ mole of $NH_3$ can be detected with ordinary laboratory instrumentation.

Other gases that were tested and found to be responsive included HCl and $CO_2$.

TABLE 1

Peak Current Response For Trimethylammine Vapor At 54° C.

| $\Delta 1$ $10^{-8}$ Amp | Field $10^6$ V/cm |
| --- | --- |
| 0.4 | 3.0 |
| 1.7 | 5.1 |
| 2.5 | 6.2 |
| 3.3 | 7.8 |

50 μl injection, 0.1 ml min$^{-1}$ flow rate

TABLE 2

Integrated Response In Coulombs For $NH_3$ Vapor At 50° C.

| Charge $10^{-9}$ Coulombs | Injection Volume Microliters |
| --- | --- |
| 4 | 25 |
| 6 | 50 |
| 12 | 100 |
| 24 | 200 |

$3 \times 10^{-6}$ V cm$^{-2}$

Industrial Applicability

The present invention provides a microdevice 10 useful for sensing the presence of any of a number of different gases. It can be used as, inter alia, a gas chromatography detector for gases that ionize in liquids. The microdevice 10 is characterized by very low power requirement and very high sensitivity.

While the invention has been described in connection with specific embodiments thereof, it will be understood that it is capable of further modification, and this application is intended to cover any variations, uses, or adaptations of the invention following, in general, the principles of the invention and including such departures from the present disclosure as come within known or customary practice in the art to which the invention pertains and as may be applied to the essential features hereinbefore set forth, and as fall within the scope of the invention and the limits of the appended claims.

I claim:

1. A microdevice for gas and vapor sensing, comprising:
   an electrically conductive substrate having an electrical insulator layer on a surface thereof, the insulator layer having an opening therethrough exposing a portion of said surface;
   electrically conducting member in contact with said insulator layer and in covering relation to said opening, said member, said insulator layer and said portion of said surface defining an ionization chamber;
   means for flowing gas through said ionization chamber;
   means for applying a voltage difference between said substrate and said member; and
   means for measuring the current flowing between said substrate and said member.

2. A microdevice as set forth in claim 1, wherein said substrate comprises a semiconductor material.

3. A microdevice as set forth in claim 2, wherein said member comprises a semiconductor material.

4. A microdevice as set forth in claim 1, wherein said insulator layer is no more than about 10,000 Angstroms thick.

5. A microdevice as set forth in claim 1, wherein said substrate is silicon or silicon carbide.

6. A microdevice as set forth in claim 5, wherein said insulator layer is silicon dioxide or silicon nitride.

7. A microdevice as set forth in claim 5, wherein said insulator layer is no more than about 10,000 Angstroms thick.

8. A microdevice as set forth in claim 7, wherein said member comprises a semiconductor material.

9. A microdevice as set forth in claim 8, wherein said substrate and said member are silicon and said insulator layer is silicon dioxide.

10. A microdevice as set forth in claim 1, wherein said insulator layer is of a thickness selected and said means for applying a voltage difference applies a voltage sufficient so as to provide an electric field strength between said substrate and said member across said opening of at least about $10^5$ volts per centimeter.

11. A microdevice as set forth in claim 10, wherein said substrate comprises a semiconductor material.

12. A microdevice as set forth in claim 11, wherein said member comprises a semiconductor material.

13. A microdevice as set forth in claim 12, wherein said substrate is silicon or silicon carbide.

14. A microdevice as set forth in claim 13, wherein said insulator layer is silicon dioxide or silicon nitride.

15. A microdevice as set forth in claim 14, wherein said substrate and said material are silicon and said insulator layer is silicon dioxide.

16. A microdevice as set forth in claim 1, wherein said ionization chamber has walls defined by said member, said insulator layer and said portion of said surface, and further including:
   a liquid film on said walls.

17. A microdevice as set forth in claim 16, wherein said film is from about 10 to about 200 Angstroms thick.

18. A microdevice as set forth in claim 1, wherein said voltage difference applying means applies a voltage difference of at least about $10^4$ V/cm.

19. A microdevice for gas and vapor sensing, comprising:
   an electrically conductive substrate having a substrate surface;
   an electrically conducting member having a member surface generally parallel to said substrate surface;
   an electrical insulator sandwiched between and abutting said substrate surface and said member surface, said insulator having an opening therethrough exposing facing portions of said substrate and member surfaces, said insulator and said facing portions of said substrate and member surfaces defining an ionization chamber;
   means for flowing gas through said chamber;
   means for applying a sufficient voltage difference between said substrate and said member to provide a voltage gradient therebetween of at least about $10^4$ V/cm and to cause a current to flow between said substrate and said member; and means for measuring the current flowing between said substrate and said member.

20. A microdevice as set forth in claim 19, wherein said insulator is no more than about 10,000 Angstroms thick.

21. A microdevice as set forth in claim 20, wherein said ionization chamber has walls defined by said member, said insulator layer and said portion of said surface, and further including:

a liquid film on said walls.

22. A microdevice as set forth in claim 21, wherein said film is from about 10 to about 200 Angstroms thick.

23. A microdevice as set forth in claim 22, wherein said substrate is silicon or silicon carbide.

* * * * *